US011779297B2

(12) United States Patent
Nakayama et al.

(10) Patent No.: US 11,779,297 B2
(45) Date of Patent: Oct. 10, 2023

(54) CONTROL DEVICE, CONTROL METHOD, AND CONTROL PROGRAM

(71) Applicant: FUJIFILM CORPORATION, Tokyo (JP)

(72) Inventors: Hiroki Nakayama, Kanagawa (JP); Tomoki Inoue, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 44 days.

(21) Appl. No.: 17/485,528

(22) Filed: Sep. 27, 2021

(65) Prior Publication Data

US 2022/0096036 A1    Mar. 31, 2022

(30) Foreign Application Priority Data

Sep. 28, 2020    (JP) .................. 2020-162699

(51) Int. Cl.
*A61B 6/00*            (2006.01)
(52) U.S. Cl.
CPC .............. *A61B 6/54* (2013.01); *A61B 6/4021* (2013.01); *A61B 6/481* (2013.01); *A61B 6/482* (2013.01); *A61B 6/502* (2013.01)
(58) Field of Classification Search
CPC ......... A61B 6/025; A61B 6/481; A61B 6/482; A61B 6/502
See application file for complete search history.

(56) References Cited

U.S. PATENT DOCUMENTS

2012/0238870 A1*  9/2012  Smith .................... A61B 6/466
                                                            600/431
2018/0235564 A1    8/2018  Jain et al.

FOREIGN PATENT DOCUMENTS

| JP | 2004-261306 A | 9/2004 |
|---|---|---|
| JP | 2007-165081 A | 6/2007 |
| JP | 2014-507250 A | 3/2014 |
| JP | 2014-151009 A | 8/2014 |
| JP | 2018-134417 A | 8/2018 |

OTHER PUBLICATIONS

English language translation of the following: Office action dated May 16, 2023 from the JPO in a Japanese patent application No. 2020-162699 corresponding to the instant patent application. This office action translation is submitted now in order to supplement the understanding of the cited references which are being disclosed in the instant Information Disclosure Statement.

* cited by examiner

*Primary Examiner* — Dani Fox
(74) *Attorney, Agent, or Firm* — SOLARIS Intellectual Property Group, PLLC

(57) ABSTRACT

A control device includes a processor that controls a mammography apparatus that irradiates a breast with radiation to capture a radiographic image of the breast such that the radiation with either first energy or second energy higher than the first energy is emitted at each of irradiation positions having different irradiation angles while a radiation source is being moved to capture low-energy projection images with the first energy and high-energy projection images with the second energy, an irradiation time for which the radiation with the second energy is emitted is longer than an irradiation time for which the radiation with the first energy is emitted, and a focus size of the radiation source in a case in which the radiation with the first energy is emitted is larger than a focus size of the radiation source in a case in which the radiation with the second energy is emitted.

8 Claims, 10 Drawing Sheets

CONTROL DEVICE, CONTROL METHOD, AND CONTROL PROGRAM

CROSS-REFERENCE TO RELATED APPLICATION

The present application claims priority under 35 U.S.C. § 119 to Japanese Patent Application No. 2020-162699 filed on Sep. 28, 2020. The above application is hereby expressly incorporated by reference, in its entirety, into the present application.

BACKGROUND

Technical Field

The present disclosure relates to a control device, a control method, and a control program.

Description of the Related Art

Contrast imaging which irradiates an object into which a contrast medium is injected with radiation having different energy levels to capture a low-energy image and a high-energy image is performed to generate a difference image indicating a difference between the high-energy image and the low-energy image. The generated difference image is an image in which the body tissues of the object have been removed and the contrast medium is clearly shown.

In addition, so-called tomosynthesis imaging which sequentially emits radiation at each of a plurality of irradiation positions having different irradiation angles and captures a plurality of projection images with a radiation detector at each irradiation position is known as a method capturing a radiographic image. JP2014-507250A discloses a mammography apparatus that can perform contrast imaging and tomosynthesis imaging.

SUMMARY

However, in some cases, in the capture of the high-energy image, the irradiation time of radiation is longer than that in the capture of the low-energy image. In this case, in a case in which the tomosynthesis imaging is performed while the radiation source is being moved, there is a large difference between the degrees of blur of the captured low-energy projection image and high-energy projection image. As a result, the quality of the generated tomographic image may deteriorate.

The present disclosure has been made in view of the above-mentioned problems, and an object of the present disclosure is to provide a control device, a control method, and a control program that can suppress a difference between the degrees of blur of a low-energy projection image and a high-energy projection image.

In order to achieve the above object, according to a first aspect of the present disclosure, there is provided a control device comprising at least one processor. The processor controls a mammography apparatus that irradiates a breast, into which a contrast medium is injected, with radiation from a radiation source to capture a radiographic image of the breast such that the radiation with either first energy or second energy higher than the first energy is emitted at each of a plurality of irradiation positions having different irradiation angles while the radiation source is being moved to capture a plurality of low-energy projection images based on the radiation with the first energy and a plurality of high-energy projection images based on the radiation with the second energy, an irradiation time for which the radiation with the second energy is emitted is longer than an irradiation time for which the radiation with the first energy is emitted, and a focus size of the radiation source in a case in which the radiation with the first energy is emitted is larger than a focus size of the radiation source in a case in which the radiation with the second energy is emitted.

According to a second aspect of the present disclosure, in the control device according to the first aspect, the processor may perform control such that a substantial focus size in a case in which the radiation with the first energy is emitted is equal to a substantial focus size in a case in which the radiation with the second energy is emitted.

According to a third aspect of the present disclosure, in the control device according to the second aspect, the substantial focus size may be determined by the focus size of the radiation source, a movement speed of the radiation source, and the irradiation time of the radiation.

According to a fourth aspect of the present disclosure, in the control device according to the first aspect, the plurality of irradiation positions may include an irradiation position where the irradiation angle along a normal direction to an imaging table on which the breast is positioned is 0 degrees, and the processor may perform control such that the radiation with the first energy is emitted at the irradiation position where the irradiation angle is 0 degrees.

According to a fifth aspect of the present disclosure, in the control device according to the first aspect, the processor may perform control such that the radiation with the second energy is emitted at an irradiation position which is a start position among the plurality of irradiation positions to capture the high-energy projection image and may derive the focus size of the radiation source in a case in which the radiation with the first energy is emitted from an amount of blur of the high-energy projection image.

According to a sixth aspect of the present disclosure, in the control device according to the first aspect, the processor may acquire the plurality of low-energy projection images and the plurality of high-energy projection images and may generate tomographic difference images indicating differences between high-energy tomographic images generated by reconstructing the plurality of high-energy projection images and low-energy tomographic images generated by reconstructing the plurality of low-energy projection images.

Further, in order to achieve the above object, according to a seventh aspect of the present disclosure, there is provided a control method comprising: controlling a mammography apparatus that irradiates a breast, into which a contrast medium is injected, with radiation from a radiation source to capture a radiographic image of the breast such that the radiation with either first energy or second energy higher than the first energy is emitted at each of a plurality of irradiation positions having different irradiation angles while the radiation source is being moved to capture a plurality of low-energy projection images based on the radiation with the first energy and a plurality of high-energy projection images based on the radiation with the second energy, an irradiation time for which the radiation with the second energy is emitted is longer than an irradiation time for which the radiation with the first energy is emitted, and a focus size of the radiation source in a case in which the radiation with the first energy is emitted is larger than a focus size of the radiation source in a case in which the radiation with the second energy is emitted.

Furthermore, in order to achieve the above object, according to an eighth aspect of the present disclosure, there is provided a non-transitory computer-readable storage medium storing a control program that causes a computer to perform a process of: controlling a mammography apparatus that irradiates a breast, into which a contrast medium is injected, with radiation from a radiation source to capture a radiographic image of the breast such that the radiation with either first energy or second energy higher than the first energy is emitted at each of a plurality of irradiation positions having different irradiation angles while the radiation source is being moved to capture a plurality of low-energy projection images based on the radiation with the first energy and a plurality of high-energy projection images based on the radiation with the second energy, an irradiation time for which the radiation with the second energy is emitted is longer than an irradiation time for which the radiation with the first energy is emitted, and a focus size of the radiation source in a case in which the radiation with the first energy is emitted is larger than a focus size of the radiation source in a case in which the radiation with the second energy is emitted.

According to the present disclosure, it is possible to suppress a difference between the degrees of blur of a low-energy projection image and a high-energy projection image.

BRIEF DESCRIPTION OF THE DRAWINGS

Exemplary embodiments according to the technique of the present disclosure will be described in detail based on the following figures, wherein.

DETAILED DESCRIPTION

Hereinafter, embodiments of the present disclosure will be described in detail with reference to the drawings. In addition, each of the embodiments does not limit the present disclosure.

Figure 1:
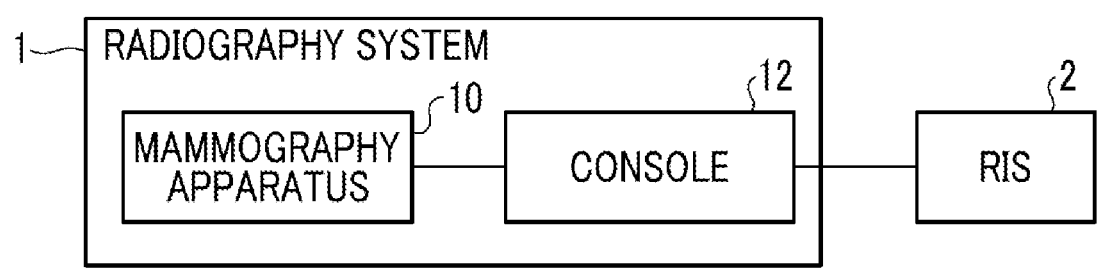
FIG. 1 is a diagram schematically illustrating an example of the overall configuration of a radiography system according to an embodiment.

First, an example of the overall configuration of a radiography system according to an embodiment will be described. FIG. 1 is a diagram illustrating an example of the overall configuration of a radiography system 1 according to this embodiment. As illustrated in FIG. 1, the radiography system 1 according to this embodiment comprises a mammography apparatus 10 and a console 12. Further, the console 12 according to this embodiment is an example of a control device according to the present disclosure.

Figure 2A:
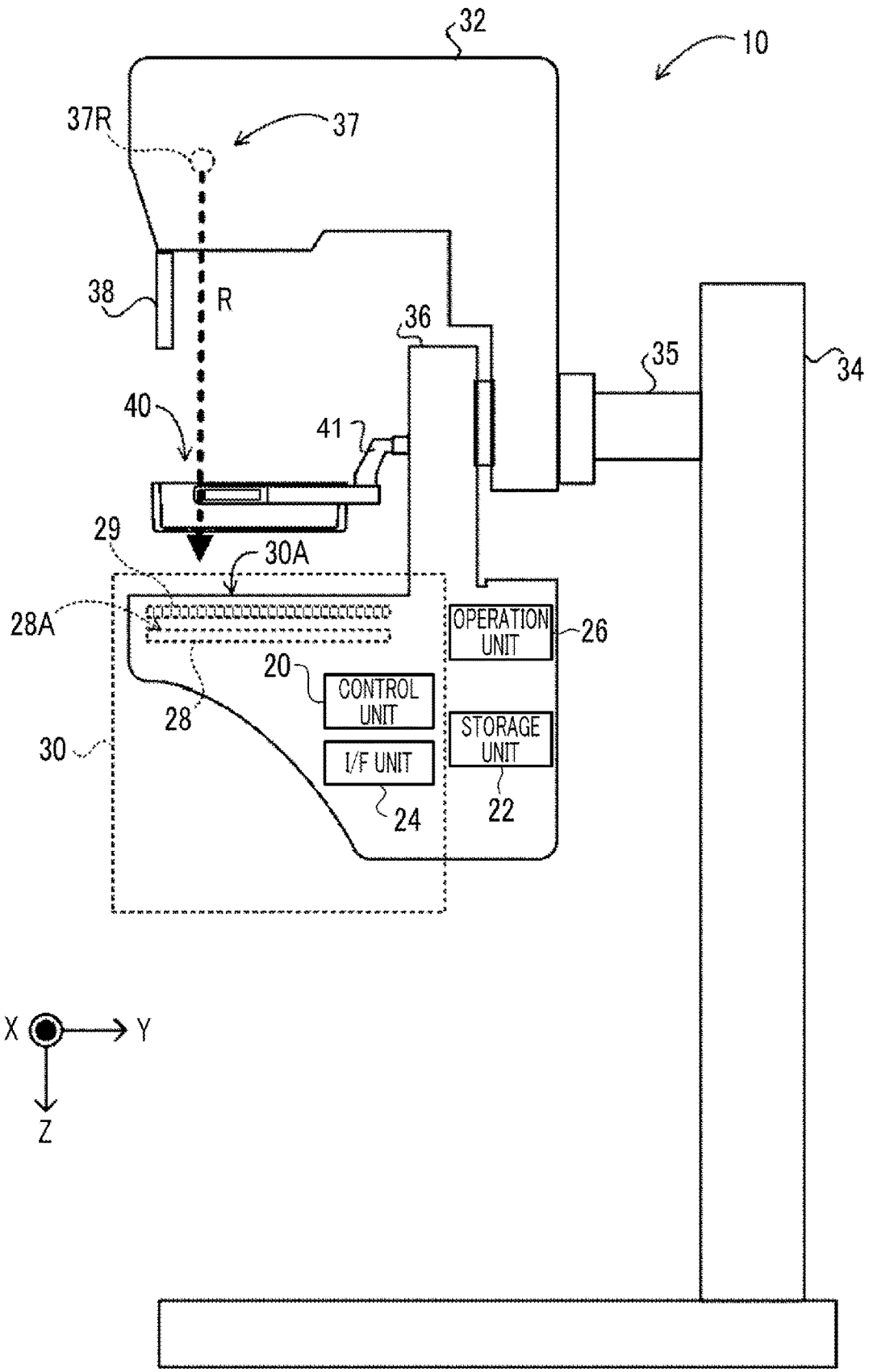
FIG. 2A is a side view illustrating an example of the outward appearance of a mammography apparatus according to the embodiment.

First, the mammography apparatus 10 according to this embodiment will be described. FIG. 2A is a side view illustrating an example of the outward appearance of the mammography apparatus 10 according to this embodiment. In addition, FIG. 2A illustrates an example of the outward appearance of the mammography apparatus 10 as viewed from the right side of a subject.

The mammography apparatus 10 according to this embodiment irradiates the breast of the subject as an object with radiation R (for example, X-rays) to capture a radiographic image of the breast. In addition, the mammography apparatus 10 may be an apparatus that captures the image of the breast of the subject not only in a state in which the subject stands up (standing state) but also in a state in which the subject sits on, for example, a chair (including a wheelchair) (sitting state).

Further, the mammography apparatus 10 according to this embodiment performs two types of imaging, that is, so-called contrast imaging that is performed in a state in which a contrast medium is injected into the breast of the subject and general imaging that is performed without using the contrast medium. In addition, in this embodiment, imaging that is performed in a state in which the contrast medium injected into the breast of the subject is referred to as "contrast imaging", and imaging other than the contrast imaging is referred to as "general imaging". Further, the mammography apparatus 10 according to this embodiment has a function of performing so-called tomosynthesis imaging which is performed while a radiation source 37R is moved to each of a plurality of irradiation positions. In addition, the mammography apparatus 10 can perform both the contrast imaging and the general imaging in the tomosynthesis imaging.

As illustrated in FIG. 2A, the mammography apparatus 10 according to this embodiment comprises a control unit 20, a storage unit 22, and an interface (I/F) unit 24 which are provided in an imaging table 30. The control unit 20 controls the overall operation of the mammography apparatus 10 under the control of the console 12. The control unit 20 comprises a central processing unit (CPU), a read only memory (ROM), and a random access memory (RAM) which are not illustrated. For example, various programs including an imaging processing program which is executed by the CPU and is used to perform control related to the capture of radiographic images are stored in the ROM in advance. The RAM temporarily stores various kinds of data.

For example, image data of the radiographic image captured by a radiation detector 28 and various other kinds of information are stored in the storage unit 22. Specific examples of the storage unit 22 include a hard disk drive (HDD) and a solid state drive (SSD). The I/F unit 24 transmits and receives various kinds of information to and from the console 12 using wireless communication or wired communication. The image data of the radiographic image captured by the radiation detector 28 in the mammography apparatus 10 is transmitted to the console 12 through the I/F unit 24 by wireless communication or wired communication.

In addition, an operation unit 26 is provided as a plurality of switches in, for example, the imaging table 30 of the mammography apparatus 10. Further, the operation unit 26 may be provided as a touch panel switch or may be provided as a foot switch that is operated by the feet of the user such as a doctor or a radiology technician.

The radiation detector 28 detects the radiation R transmitted through the breast which is an object. As illustrated in FIG. 2A, the radiation detector 28 is disposed in an imaging table 30. In the mammography apparatus 10 according to this embodiment, in a case in which imaging is performed, the breast of the subject is positioned on an imaging surface 30A of the imaging table 30 by the user.

The radiation detector 28 detects the radiation R transmitted through the breast of the subject and the imaging table 30, generates a radiographic image on the basis of the detected radiation R, and outputs image data indicating the generated radiographic image. The type of the radiation detector 28 according to this embodiment is not particularly limited. For example, the radiation detector 28 may be an indirect-conversion-type radiation detector that converts the radiation R into light and converts the converted light into charge or a direct-conversion-type radiation detector that directly converts the radiation R into charge.

Figure 2B:
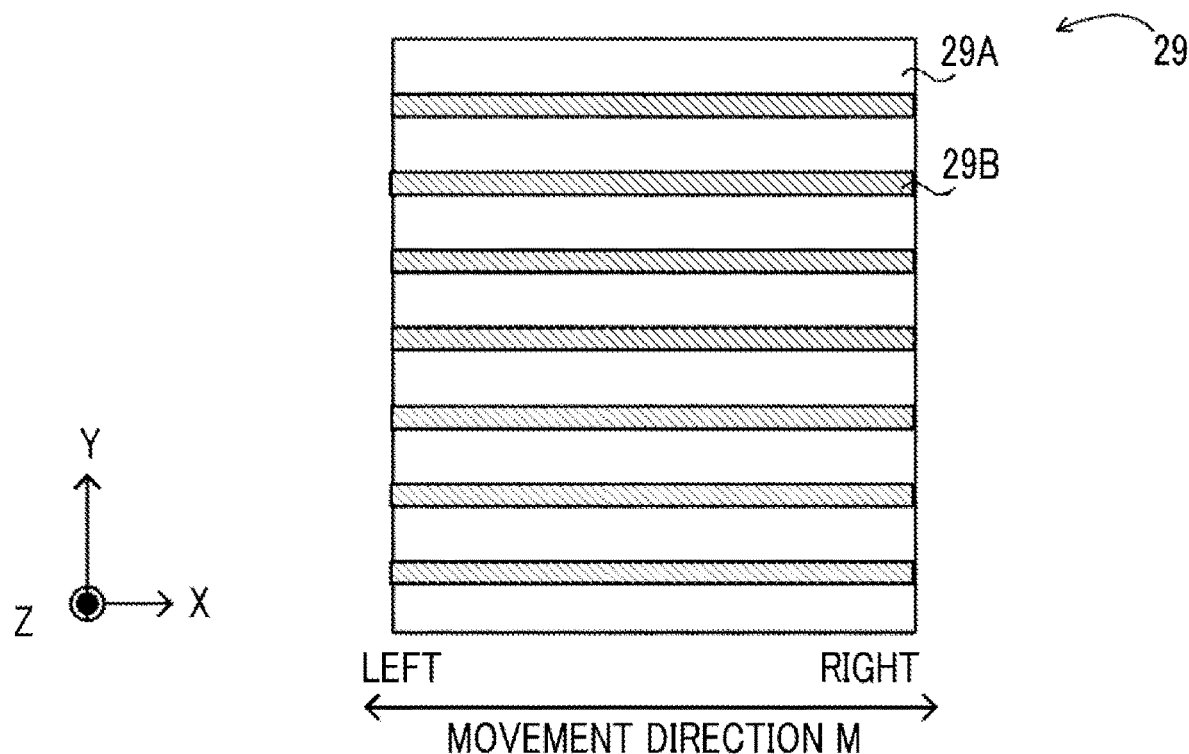
FIG. 2B is a plan view illustrating an example of a grid according to the embodiment as viewed from a radiation source.

Further, a grid 29 that removes scattered rays caused by the radiation transmitted through the breast is disposed in the imaging table 30. Specifically, as illustrated in FIG. 2A, the grid 29 is disposed between the radiation detector 28 and the imaging surface 30A of the imaging table 30. FIG. 2B is a plan view illustrating an example of the grid 29 according to this embodiment as viewed from the radiation source 37R.

As illustrated in FIG. 2B, the grid 29 comprises a transmission portion 29A that transmits the radiation R and an absorption portion 29B that absorbs the radiation. The transmission portion 29A and the absorption portion 29B are disposed in the imaging table 30 so as to extend in the left-right direction of the subject positioned on the imaging table 30. As illustrated in FIG. 2B, in the grid 29, the transmission portion 29A and the absorption portion 29B are alternately disposed in a direction (the front-rear direction of the subject) orthogonal to the left-right direction. In the mammography apparatus 10 according to this embodiment, in a case in which the tomosynthesis imaging is performed, the radiation source 37R of a radiation emitting unit 37 is moved in the left-right direction of the subject positioned on the imaging table 30, which will be described below. That is, in the grid 29 according to this embodiment, the transmission portion 29A and the absorption portion 29B are alternately arranged in a direction intersecting a movement direction M in which the radiation source 37R is moved.

An example of the material forming the absorption portion 29B is a lead thin film. Further, examples of the material forming the transmission portion 29A include aluminum, paper, and carbon fiber. As a tube voltage of the radiation source 37R becomes higher, the number of scattered rays tends to become larger. In addition, as a grid ratio becomes higher, it is more effective to reduce the scattered rays. Therefore, the grid ratio of the grid 29 is determined according to, for example, the tube voltage of the radiation source 37R used.

As described above, in the grid 29 according to this embodiment, the transmission portion 29A and the absorption portion 29B are alternately arranged in the direction intersecting the movement direction M in which the radiation source 37R is moved. Therefore, according to the grid 29 of this embodiment, in a case in which the tomosynthesis imaging is performed, the scattered rays can be suppressed without being affected by the oblique incidence of the radiation R on the imaging table 30.

Figure 2C:
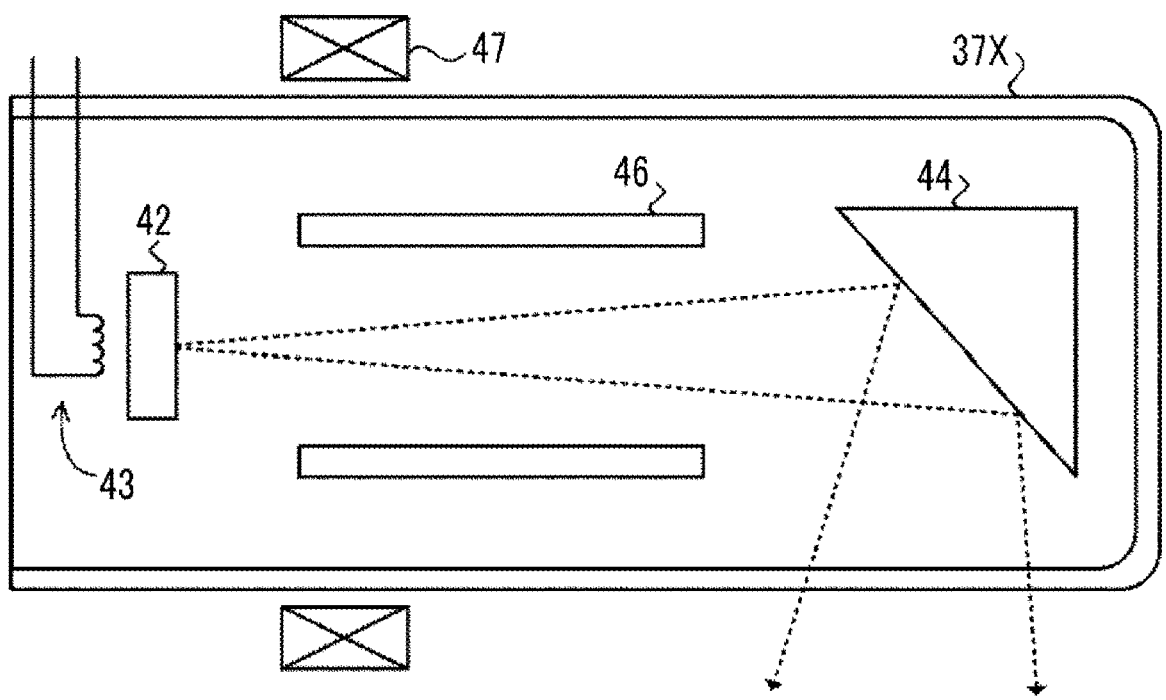
FIG. 2C is a side view illustrating an example of a radiation tube according to the embodiment.
Figure 2D:
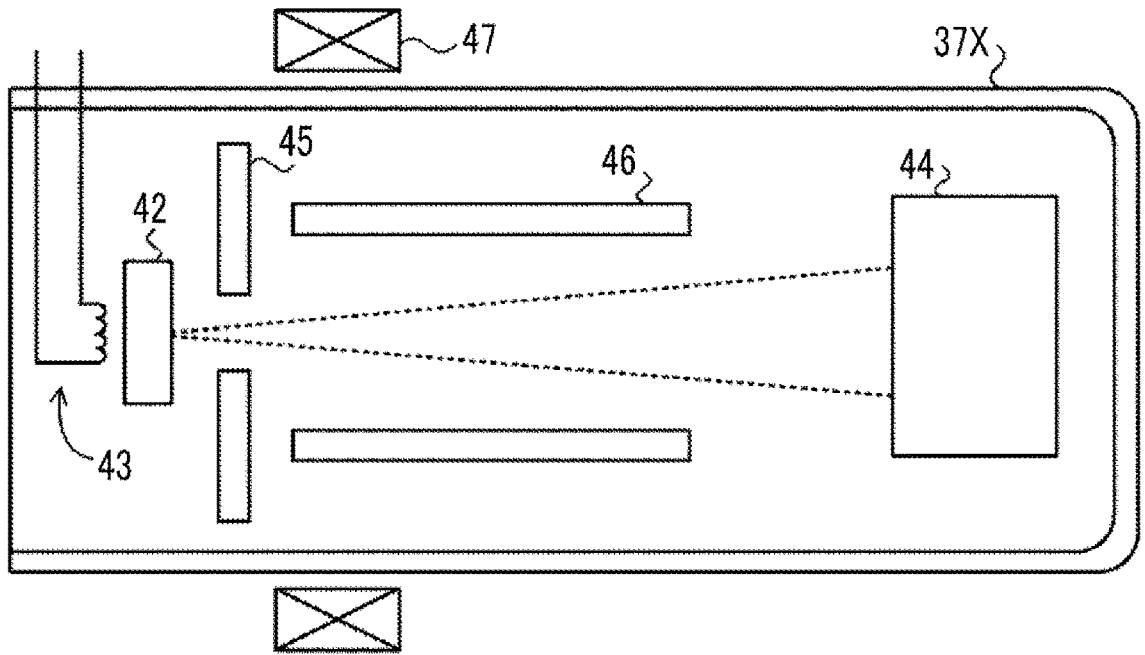
FIG. 2D is a plan view illustrating the radiation tube according to the embodiment as viewed from the upper side.

The radiation emitting unit 37 comprises the radiation source 37R. The radiation source 37R according to this embodiment comprises a radiation tube 37X illustrated in FIGS. 2C and 2D as an example. FIG. 2C is a side view illustrating the radiation tube 37X, and FIG. 2D is a plan view illustrating the radiation tube 37X as viewed from the upper side. As illustrated in FIGS. 2C and 2D, the radiation tube 37X according to this embodiment comprises a cathode 42, a heater 43, an anode 44, a grid electrode 45, a focusing electrode 46, and an electrode coil 47.

The cathode 42 and the anode 44 are disposed at opposite positions. Electrons are emitted from the cathode 42 to the anode 44. In a case in which the electrons collide with the anode 44, radiation is emitted from the anode 44. The grid electrode 45 having an opening portion and the focusing electrode 46 having a cylindrical shape are disposed between the cathode 42 and the anode 44. The cathode 42 is heated by the heater 43 to emit an electron beam. The electron beam emitted from the cathode 42 collides with the anode 44 through the grid electrode 45 and the focusing electrode 46. The electrons emitted from the cathode 42 collide with the anode 44 through the opening portion of the grid electrode 45 and the cylinder of the focusing electrode 46. In addition, the electrode coil 47 for changing the electron beam is provided outside the radiation tube 37X and is supplied with a deflection current from a radiation source control unit (not illustrated) provided in the radiation emitting unit 37. The radiation source control unit controls a focus voltage between the cathode 42 and the focusing electrode 46 and the deflection current supplied to the electrode coil 47 to control the potential of the grid electrode 45. The potential of the grid electrode 45 is controlled to control the width of the electron beam (corresponding to the length in the X-axis direction and the length of the subject in the left-right direction) passing through the opening portion of the grid electrode 45. As a result, the area corresponding to the anode 44 is controlled. The area of the electron beam that hits the anode 44 corresponds to the focus size of the radiation source 37R. That is, in the radiation source 37R according to this embodiment, the potential of the grid electrode 45 of the radiation tube 37X can be controlled to control the focus size. In addition, the configuration for making the focus size of the radiation source 37R variable is not limited to the aspect described in this embodiment.

Further, as illustrated in FIG. 2A, the radiation emitting unit 37 is provided in an arm portion 32 together with the imaging table 30 and a compression unit 36. As illustrated in FIG. 2A, a face guard 38 is attachably and detachably provided at a position of the arm portion 32 which is close to the subject below the radiation emitting unit 37. A face guard 38 is a protective member for protecting the subject from the radiation R emitted from the radiation source 37R.

In addition, as illustrated in FIG. 2A, the mammography apparatus 10 according to this embodiment comprises the arm portion 32, a base 34, and a shaft portion 35. The arm portion 32 is held by the base 34 so as to be movable in the up-down direction (Z-axis direction). Further, the arm portion 32 can be rotated with respect to the base 34 by the shaft portion 35. The shaft portion 35 is fixed to the base 34 such that the shaft portion 35 and the arm portion 32 are rotated integrally.

Gears are provided in each of the shaft portion 35 and the compression unit 36. The gears can be switched between an engaged state and a non-engaged state to switch between a state in which the compression unit 36 and the shaft portion 35 are connected and rotated integrally and a state in which the shaft portion 35 is separated from the compression unit 36 and the imaging table 30 and runs idle. In addition, components for switching between the transmission and non-transmission of the power of the shaft portion 35 are not limited to the gears, and various mechanical elements may be used.

Each of the arm portion 32, the imaging table 30, and the compression unit 36 can be relatively rotated with respect to the base 34, using the shaft portion 35 as a rotation axis. In this embodiment, engagement portions (not illustrated) are provided in each of the base 34, the arm portion 32, the imaging table 30, and the compression unit 36. The state of the engagement portions is switched to connect each of the arm portion 32, the imaging table 30, and the compression unit 36 to the base 34. The arm portion 32, the imaging table 30, and the compression unit 36 connected to the shaft portion 35 are integrally rotated on the shaft portion 35.

The compression unit 36 is provided with a compression plate driving unit (not illustrated) that moves a compression plate 40 in the up-down direction (Z-axis direction). The compression plate 40 according to this embodiment has a function of compressing the breast of the subject. A support portion 41 of the compression plate 40 is detachably attached to the compression plate driving unit and is moved in the up-down direction (Z-axis direction) by the compression plate driving unit to compress the breast of the subject between the compression plate 40 and the imaging table 30. The compression plate 40 according to this embodiment is an example of a compression member according to the present disclosure.

Figure 2E:
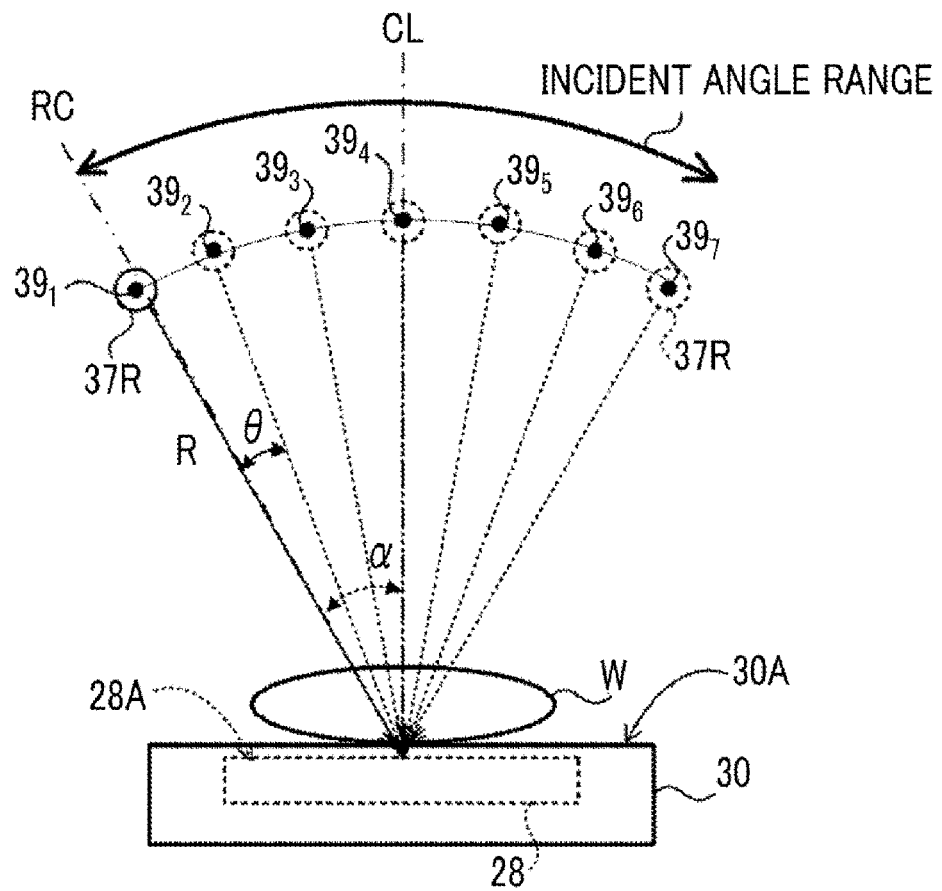
FIG. 2E is a diagram illustrating an example of tomosynthesis imaging.

In a case in which the mammography apparatus 10 performs the tomosynthesis imaging, the radiation source 37R of the radiation emitting unit 37 is moved in the left-right direction of the subject positioned on the imaging table 30. Specifically, the radiation source 37R is continuously moved to each of a plurality of irradiation positions having different irradiation angles by the rotation of the arm portion 32. FIG. 2E is a diagram illustrating an example of the tomosynthesis imaging. In addition, the compression plate 40 is not illustrated in FIG. 2E. In this embodiment, as illustrated in FIG. 2E, the radiation source 37R is moved to a plurality of irradiation positions $39_1$ to $39_7$ having different irradiation angles that are arranged at a predetermined interval of an angle $\theta$. In other words, the radiation source 37R is moved to the positions where the incident angles of the radiation R on the detection surface 28A of the radiation detector 28 are different. In addition, hereinafter, in a case in which the irradiation positions $39_1$ to $39_7$ are generically referred to without being specifically distinguished from each other, they are referred to as irradiation positions 39. Further, in this embodiment, as illustrated in FIG. 2E as an example, the aspect in which the number of irradiation positions is 7 and imaging is performed seven times in the tomosynthesis imaging will be described. However, the irradiation position (irradiation angle) or the number of irradiation positions (the number of imaging operations) in the tomosynthesis imaging is not limited to this embodiment.

At the irradiation positions 39, the radiation R is emitted from the radiation source 37R to a breast W in response to an instruction from the console 12, and the radiation detector 28 captures a radiographic image. In addition, hereinafter, in the tomosynthesis imaging, the radiographic images captured by the radiation detector 28 at a plurality of irradiation positions 39 having different irradiation angles are referred to as "projection images". In a case in which the radiography system 1 performs the tomosynthesis imaging that moves the radiation source 37R to each irradiation position 39 and captures the projection image at each irradiation position 39, seven projection images are obtained. In addition, hereinafter, in a case in which a plurality of types of radiographic images, such as projection images and tomographic images, are generically referred to, they are simply referred to as "radiographic images".

In addition, as illustrated in FIG. 2E, the incident angle of the radiation R means the angle $\alpha$ formed between a normal line CL to the detection surface 28A of the radiation detector 28 and a radiation axis RC. Further, here, the detection surface 28A of the radiation detector 28 is a surface that is substantially parallel to the imaging surface 30A. Hereinafter, a predetermined range in which the incident angles are different in the tomosynthesis imaging as illustrated in FIG. 2E is referred to as an "incident angle range". A specific example of the incident angle range is a range of ±10 degrees or ±20 degrees with respect to the normal line CL to the detection surface 28A of the radiation detector 28. In this embodiment, the "incident angle" and the "irradiation angle" of the radiation R are synonymous.

The console 12 according to this embodiment has a function of controlling the mammography apparatus 10 using, for example, an imaging order and various kinds of information acquired from a radiology information system (RIS) 2 through a wireless communication local area network (LAN) and instructions input by the user through an operation unit 56 or the like.

Figure 3:
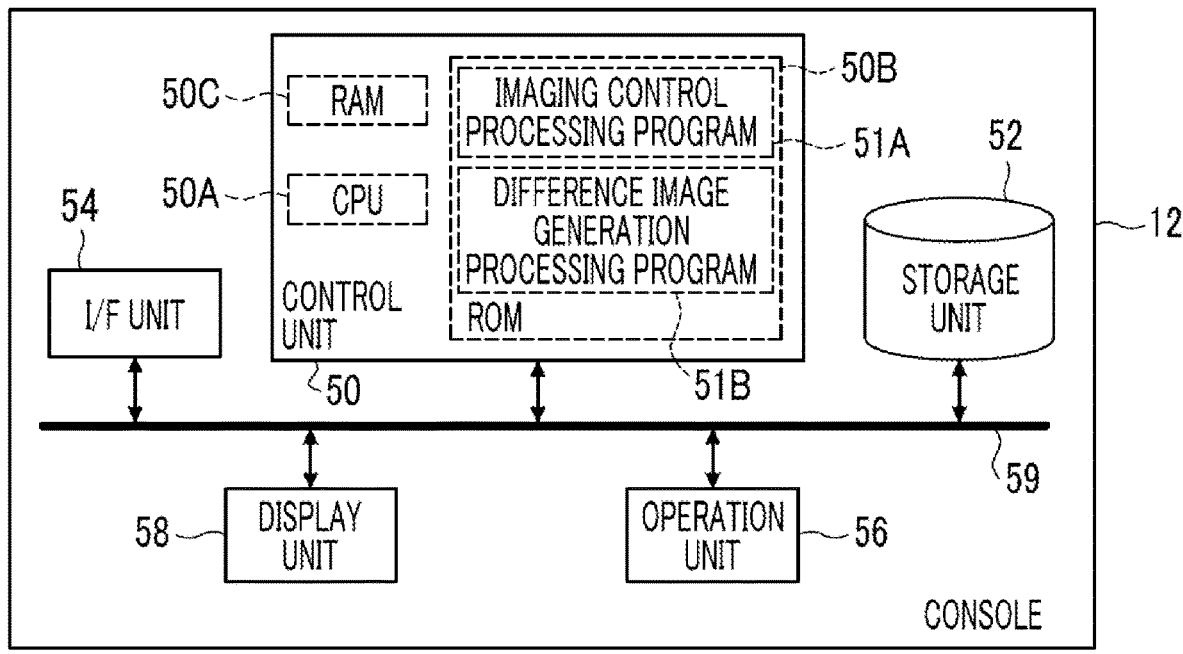
FIG. 3 is a block diagram illustrating an example of the configuration of a console according to the embodiment.

For example, the console 12 according to this embodiment is a server computer. As illustrated in FIG. 3, the console 12 comprises a control unit 50, a storage unit 52, an I/F unit 54, the operation unit 56, and a display unit 58. The control unit 50, the storage unit 52, the OF unit 54, the operation unit 56, and the display unit 58 are connected to each other through a bus 59, such as a system bus or a control bus, such that they can transmit and receive various kinds of information.

The control unit 50 according to this embodiment controls the overall operation of the console 12. The control unit 50 comprises a CPU 50A, a ROM 50B, and a RAM 50C. Various programs including an imaging control processing program 51A and a difference image generation processing program 51B, which will be described below, executed by the CPU 50A are stored in the ROM 50B in advance. The RAM 50C temporarily stores various kinds of data. The CPU 50A according to this embodiment is an example of a processor according to the present disclosure. The imaging control processing program 51A according to this embodiment is an example of a control program according to the present disclosure.

For example, the image data of the radiographic image captured by the mammography apparatus 10 and various other kinds of information are stored in the storage unit 52. An HDD or an SSD is given as a specific example of the storage unit 52.

The operation unit 56 is used by the user to input, for example, instructions which are related to the capture of a radiographic image and include an instruction to emit the radiation R or various kinds of information. The operation unit 56 is not particularly limited. Examples of the operation unit 56 include various switches, a touch panel, a touch pen, and a mouse. The display unit 58 displays various kinds of information. In addition, the operation unit 56 and the display unit 58 may be integrated into a touch panel display.

The I/F unit 54 transmits and receives various kinds of information between the mammography apparatus 10 and the RIS 2 using wireless communication or wired communication. In the radiography system 1 according to this embodiment, the console 12 receives the image data of the radiographic image captured by the mammography apparatus 10 from the mammography apparatus 10 through the I/F unit 54, using wireless communication or wired communication.

Figure 4:
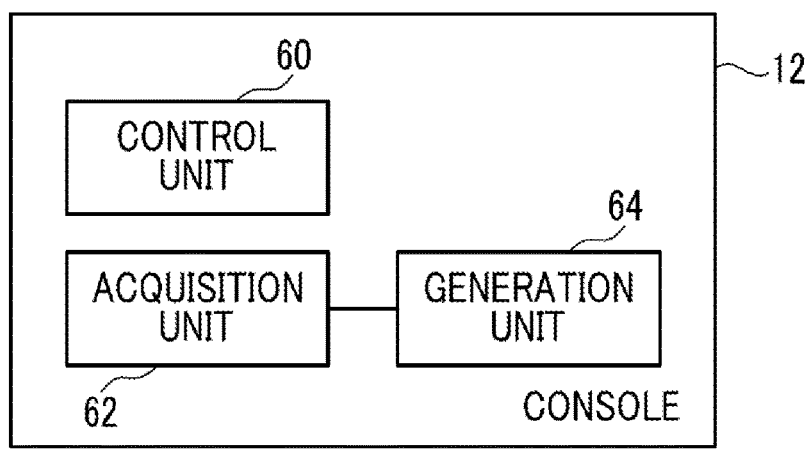
FIG. 4 is a functional block diagram illustrating an example of the function of the console according to the embodiment.

In addition, FIG. 4 is a functional block diagram illustrating an example of the configuration of the console 12 according to this embodiment. As illustrated in FIG. 4, the console 12 comprises a control unit 60. For example, in the console 12 according to this embodiment, the CPU 50A of the control unit 50 executes the imaging control processing program 51A stored in the ROM 50B to function as the control unit 60.

The control unit 60 has a function of controlling the contrast imaging and specifically has a function of performing control related to the emission of the radiation R in the contrast imaging by the mammography apparatus 10.

Further, in the case of the tomosynthesis imaging, the control unit 60 controls the mammography apparatus 10 such that either the radiation R with the first energy or the radiation R with second energy higher than the first energy is emitted to capture projection images at each of the plurality of irradiation positions 39. In this embodiment, the radiographic image captured by emitting the radiation R with the first energy is referred to as a "low-energy image" and is referred to as a "low-energy projection image" in a case in which the projection images are distinguished. Further, the radiographic image captured by emitting the radiation R with the second energy is referred to as a "high-energy image" and is referred to as a "high-energy projection image" in a case in which the projection images are distinguished.

Specifically, in the case of the tomosynthesis imaging, the control unit 60 performs control such that the radiation R with the second energy is emitted at each of the irradiation positions $39_1$, $39_3$, $39_5$, and $39_7$ to capture the high-energy projection images. Further, the control unit 60 performs control such that the radiation R with the first energy is emitted at each of the irradiation positions $39_2$, $39_4$, and $39_6$ to capture the low-energy projection images.

For example, an iodine contrast medium having a k-edge of 33 keV is generally used as the contrast medium used for the contrast imaging. In this case, in the contrast imaging, the radiation R with the first energy lower than the k-edge of the iodine contrast medium is emitted to capture the low-energy image. Further, the radiation R with the second energy higher than the k-edge of the iodine contrast medium is emitted to capture the high-energy image.

Therefore, the control unit 60 according to this embodiment performs control to direct the radiation source 37R to emit the radiation R with the first energy and control to direct the radiation source 37R to emit the radiation R with the second energy in the contrast imaging.

Radiation absorption characteristics are different between the contrast media and the body tissues such as the mammary gland. Therefore, in the high-energy image captured as described above, the body tissues, such as the mammary glands and fat, are shown and the contrast medium is clearly shown. In addition, in the low-energy image, the contrast medium is hardly shown, and the body tissues, such as the mammary glands, are clearly shown. Therefore, a difference image indicating the difference between the low-energy image and the high-energy image can be an image in which a mammary gland structure has been removed and the contrast medium is clearly shown.

Further, the control unit 60 according to this embodiment has a function of performing control such that the irradiation time for which the radiation R with the second energy is emitted is longer than the irradiation time for which the radiation R with the first energy is emitted. In the imaging performed by emitting the high-energy radiation R, a low-energy component is cut in order to move an energy distribution to the high voltage side. Therefore, for the second energy, irradiation dose efficiency is worse (lower) than that for the first energy. Further, in a case in which the difference image is generated as described above, the low-energy image is subtracted from the high-energy image. Therefore, it is preferable to increase (improve) the quality of the high-energy image. The control unit 60 according to this embodiment performs control such that the irradiation time for which the radiation R with the second energy is emitted is longer than the irradiation time for which the radiation R with the first energy is emitted to improve irradiation efficiency and to improve the quality of the high-energy image.

Further, the control unit 60 according to this embodiment performs control such that the focus size of the radiation source 37R in a case in which the radiation R with the first energy is emitted is larger than the focus size of the radiation source 37R in a case in which the radiation R with the second energy is emitted. As described above, since the irradiation time for which the radiation R with the second energy is emitted is longer than the irradiation time for which the radiation R with the first energy is emitted, the high-energy image has a stronger sense of blur than the low-energy image as it is. In the tomosynthesis imaging, the high-energy projection image is more blurred than the low-energy projection image.

In a case in which the degree of blur is different between the high-energy image and the low-energy image, the quality of the difference image indicating the difference between the high-energy image and the low-energy image deteriorates. In this embodiment, a tomographic difference image indicating a difference between a high-energy tomographic image obtained by reconstructing the high-energy projection image and a low-energy tomographic image obtained by reconstructing the low-energy projection image is generated (which will be described in detail below). Even in this configuration, in a case in which the degree of blur is different between the high-energy tomographic image and the low-energy tomographic image, the quality of the tomographic difference image deteriorates. Therefore, it is preferable that the degree of blur of the high-energy image is the same as the degree of blur of the low-energy image. In a case in which the degree of blur of the high-energy image is the same as the degree of blur of the low-energy image, the blur is offset in the difference image indicating the difference between the high-energy image and the low-energy image, and image quality is improved. Therefore, the control unit 60 performs control such that the degree of blur of the low-energy image is close to the degree of blur of the high-energy image.

In this embodiment, the radiation R is emitted while the radiation source 37R is being moved. Therefore, the substantial focus size is a value obtained by adding the moving distance of the radiation source 37R to the focus size of the radiation source 37R as represented by the following Expression (1). In addition, the moving distance of the radiation source 37R can be derived from the movement speed of the radiation source 37R and the irradiation time of the radiation R. More precisely, the moving distance of the radiation source 37R can be derived from the irradiation time of the radiation R and the distance between the rotation center of the arm portion 32 and the radiation tube 37X (focus).

Here, the focus size of the radiation source 37R is specifically the focus size of the radiation tube 37X. In addition, hereinafter, a "substantial focus size" means the focus size represented by the following Expression (1), and a "focus size" simply means the focus size of the radiation tube 37X.

$$\text{Substantial focus size=focus size+moving distance of radiation source } 37R \quad (1)$$

Therefore, the control unit 60 performs control such that the focus size in a case in which the radiation R with the first energy is emitted is larger than the focus size in a case in which the radiation R with the second energy is emitted in order to make the degree of blur of the low-energy image close to the degree of blur of the high-energy image.

In addition, it is preferable that the substantial focus size in a case in which the radiation with the first energy is emitted is equal to the substantial focus size in a case in which the radiation with the second energy is emitted. Therefore, the control unit 60 according to this embodiment performs control such that the focus size in which the radiation R with the first energy is emitted is the size derived by the following Expression (2). Further, an "imaging moving distance" in the following Expression (2) means the distance moved by the radiation source 37R while emitting the radiation R. Furthermore, the case in which the substantial focus size in the emission of the radiation with the first energy is "equal" to the substantial focus size in the emission of the radiation with the second energy is not limited to a case in which the substantial focus sizes are completely equal to each other and may be a case in which errors, such as design errors, are ignored and the substantial focus sizes are regarded as being equal to each other. For example, in a case in which the difference between the substantial focus size in the emission of the radiation with the first energy and the substantial focus size in the emission of the radiation with the second energy is within ±10%, the substantial focus sizes can be regarded as being equal to each other.

$$\begin{aligned}&\text{Focus size in emission of radiation with first}\\&\quad\text{energy=focus size in emission of radiation}\\&\quad\text{with second energy+imaging moving distance in}\\&\quad\text{emission of radiation with second energy-}\\&\quad\text{imaging moving distance in emission of radiation}\\&\quad\text{with first energy}\end{aligned} \quad (2)$$

Further, as illustrated in FIG. 4, the console 12 according to this embodiment comprises an acquisition unit 62 and a generation unit 64. In the console 12 according to this embodiment, the CPU 50A of the control unit 50 executes the difference image generation processing program 51B stored in the ROM 50B to function as the acquisition unit 62 and the generation unit 64.

The acquisition unit 62 has a function of acquiring the low-energy projection image and the high-energy projection image captured by the mammography apparatus 10. Specifically, the acquisition unit 62 acquires image data indicating each of a plurality of (in this embodiment, three) low-energy projection images and image data indicating each of a plurality of (in this embodiment, four) high-energy projection images captured by the radiation detector 28 of the mammography apparatus 10 through the I/F unit 24 and the I/F unit 54. The acquisition unit 62 outputs the acquired low-energy projection images and high-energy projection images to the generation unit 64.

Figure 5:
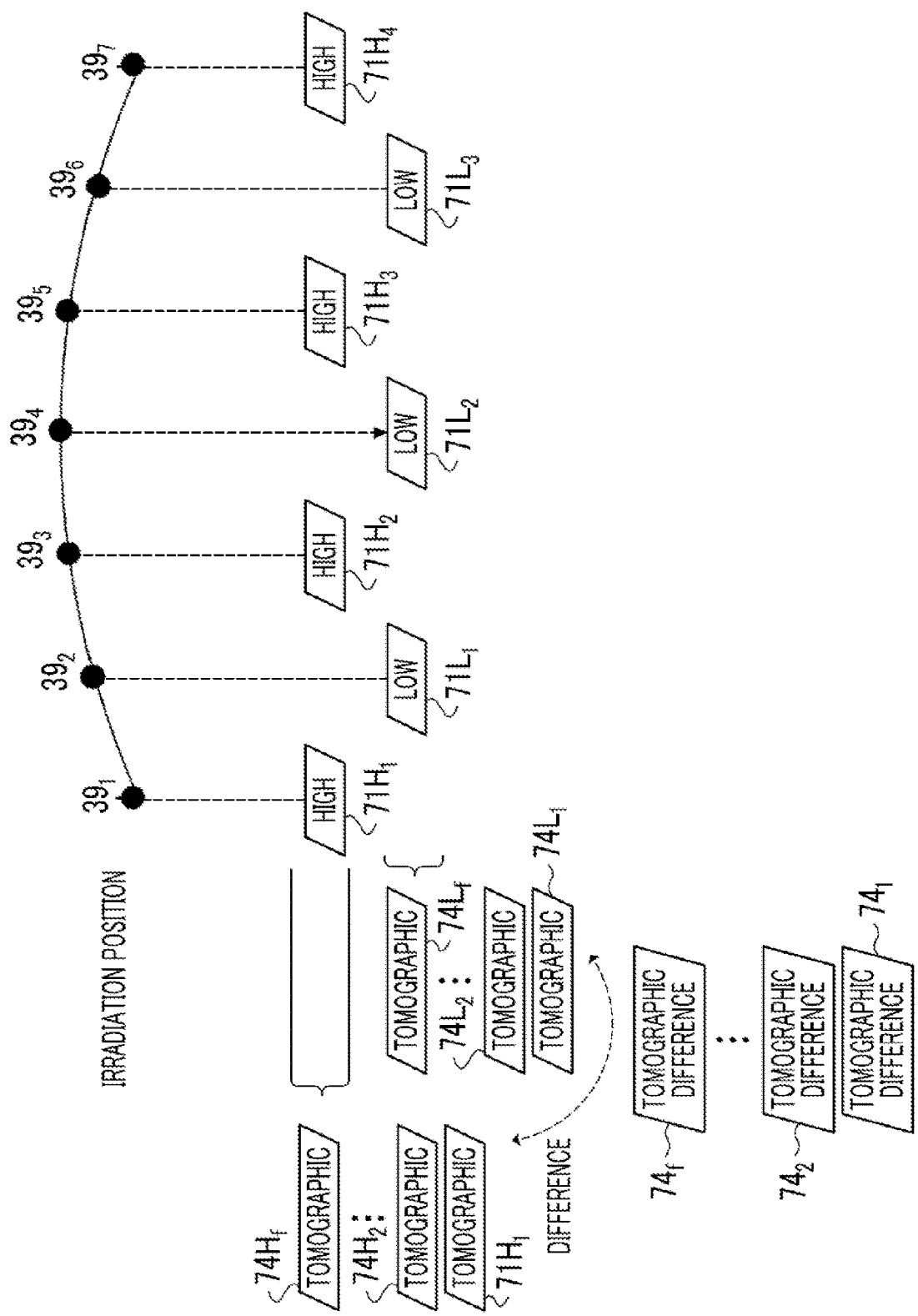
FIG. 5 is a diagram illustrating an example of a method for generating a difference image.

The generation unit 64 has a function of generating a tomographic difference image. The generation of the tomographic difference image by the generation unit 64 according to this embodiment will be described in detail with reference to FIG. 5. The generation unit 64 reconstructs low-energy projection images $71L_1$, $71L_2$, and $71L_3$ to generate a series of low-energy tomographic images 74L having a predetermined slice thickness. FIG. 5 illustrates an aspect in which flow-energy tomographic images 74L ($74L_1$ to $74L_f$) are generated from a series of low-energy projection images 71L. Further, the generation unit 64 reconstructs high-energy projection images $71H_1$, $71H_2$, $71H_3$, and $71H_4$ to generate a series of high-energy tomographic images 74H having a predetermined slice thickness. FIG. 5 illustrates an aspect in which f high-energy tomographic images 74H ($74H_1$ to $74H_f$) are generated from a series of high-energy projection images 71H. Then, the generation unit 64 generates tomographic difference images 74 ($74_1$ to $74_f$) which are difference images indicating the differences between the high-energy tomographic images 74H and the low-energy tomographic images 74L at the corresponding slice positions.

For example, in this embodiment, the difference between the high-energy tomographic image and the low-energy tomographic image at the corresponding slice position is derived to generate a tomographic difference image. Specifically, the generation unit 64 subtracts image data obtained by multiplying the low-energy tomographic image by a predetermined coefficient from image data obtained by multiplying the high-energy tomographic image by a predetermined coefficient for each corresponding pixel to generate image data of a tomographic difference image indicating a difference image in which the mammary gland tissues have been removed and the contrast medium is clearly shown. In addition, since both the low-energy tomographic image and the high-energy tomographic image are blurred, it is preferable to derive the difference after performing alignment. In particular, it is preferable to derive the difference after alignment for the region of interest. The region of interest may be specified, for example, by applying computer aided diagnosis (CAD) to each of the low-energy tomographic image and the high-energy tomographic image.

Further, a method for generating each of the low-energy tomographic image 74L and the high-energy tomographic image 74H in the generation unit 64 is not particularly limited. For example, reconstruction may be performed by a back projection method, such as a filter back projection (FBP) method or an iterative reconstruction method, or a known technique may be applied. In addition, the slice thicknesses of the low-energy tomographic image 74L and the high-energy tomographic image 74H to be generated may be the same in the two tomographic images, and the specific value of the slice thickness is not limited. The slice thickness can be determined according to, for example, the size of an object of interest, the quality of the radiographic image, the processing load of arithmetic processing in the generation, and an instruction from the user.

Next, the operation of the console 12 in the contrast imaging by the radiography system 1 according to this embodiment will be described with reference to the drawings.

Figure 6:
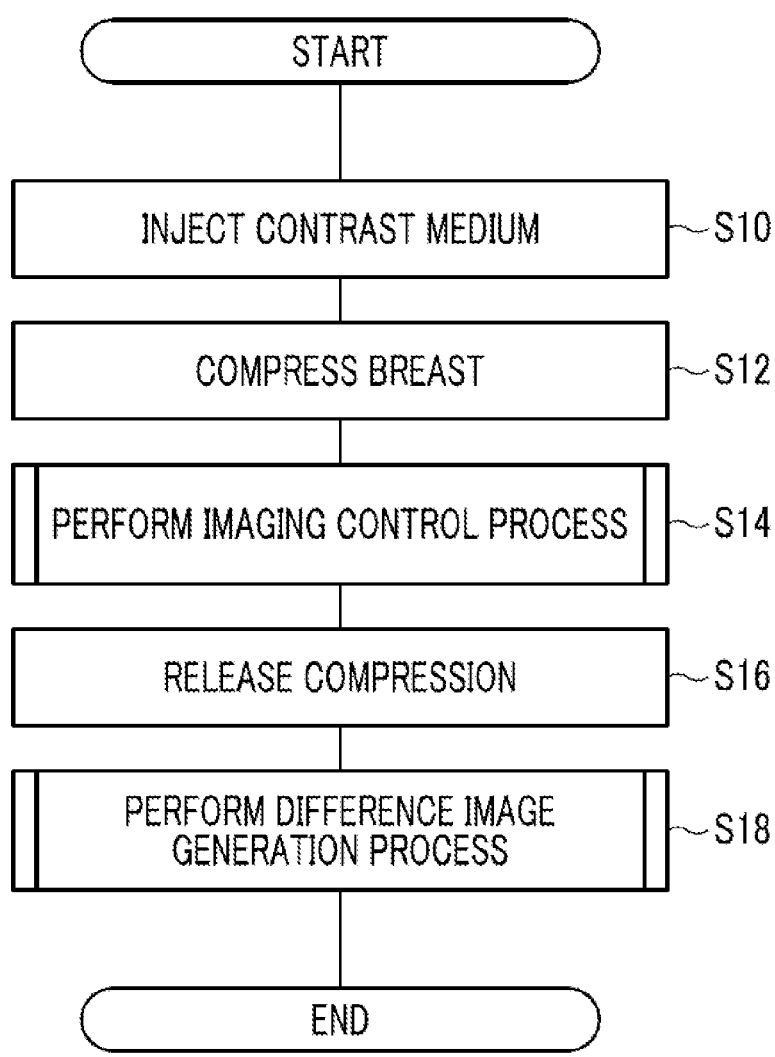
FIG. 6 is a flowchart illustrating an example of the flow of contrast imaging by the radiography system according to the embodiment.

FIG. 6 is a flowchart illustrating an example of the flow of the contrast imaging by the radiography system 1 according to this embodiment. In a case in which the contrast imaging is performed, first, the user injects the contrast medium into the breast as illustrated in Step S10 of FIG. 6. Then, as illustrated in Step S12, the user positions the breast of the subject on the imaging table 30 of the mammography apparatus 10 and compresses the breast with the compression plate 40.

Figure 7:
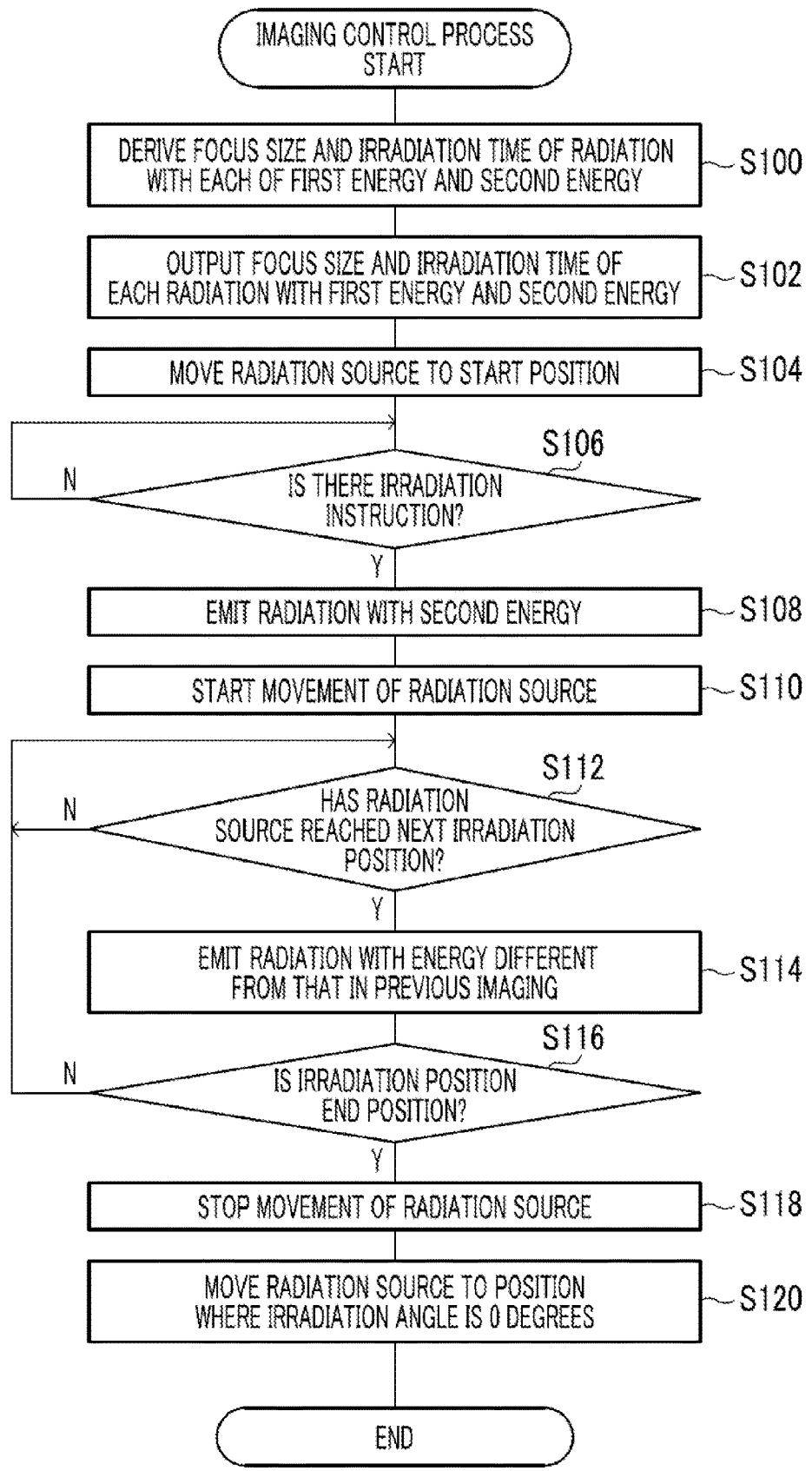
FIG. 7 is a flowchart illustrating an example of the flow of an imaging control process.

Then, in Step S14, the console 12 performs an imaging control process illustrated in FIG. 7 in order to perform the contrast imaging in the mammography apparatus 10. In the console 12 according to this embodiment, for example, the CPU 50A of the control unit 50 executes the imaging control processing program 51A stored in the ROM 50B to perform the imaging control process whose example is illustrated in FIG. 7. FIG. 7 is a flowchart illustrating an example of the flow of the imaging control process performed in the console 12 according to this embodiment.

In Step S100 of FIG. 7, the control unit 60 derives the focus size and irradiation time of the radiation R with the first energy and the focus size and irradiation time of the radiation R with the second energy as described above. In this embodiment, the focus size and irradiation time of the radiation R with the first energy and the focus size and irradiation time of the radiation R with the second energy are stored in the storage unit 52 in advance in a state in which the irradiation time of the radiation R with the second energy is longer and the focus size of the radiation R with the first energy is larger. Therefore, the control unit 60 acquires the focus size and irradiation time of the radiation R with the first energy and the focus size and irradiation time of the radiation R with the second energy from the storage unit 52 to derive them.

Then, in Step S102, the control unit 60 outputs the focus size and irradiation time of the radiation R with the first energy and the focus size and irradiation time of the radiation R with the second energy derived in Step S100 to the mammography apparatus 10. The focus size and irradiation time of the radiation R with the first energy and the focus size and irradiation time of the radiation R with the second energy input from the console 12 are set in the radiation emitting unit 37 of the mammography apparatus 10.

Then, in Step S104, the control unit 60 moves the radiation source 37R to the irradiation position which is a start position where the emission of the radiation R is started. In this embodiment, the radiation source 37R is moved to the irradiation position $39_1$.

Then, in Step S106, the control unit 60 determines whether or not an instruction to emit the radiation R is received. The determination result in Step S106 is "No" until the irradiation instruction is received. On the other hand, in a case in which the irradiation instruction is received, the determination result in Step S106 is "Yes", and the process proceeds to Step S108.

In Step S108, the control unit 60 outputs an instruction to emit the radiation R with the second energy to the mammography apparatus 10. In the mammography apparatus 10, the control unit 20 directs the radiation source 37R to emit the radiation R with the second energy to the breast on the basis of the instruction input from the console 12, and the radiation detector 28 captures a high-energy projection image. In the example illustrated in FIG. 5, the high-energy projection image $71H_1$ is captured.

Then, in Step S110, the control unit 60 starts the movement of the radiation source 37R. Then, in Step S112, the control unit 60 determines whether or not the radiation source 37R has reached the next irradiation position 39. The determination result in Step S112 is "No" until the radiation source 37R reaches the next irradiation position 39. On the other hand, in a case in which the radiation source 37R has reached the next irradiation position 39, the determination result in Step S112 is "Yes", and the process proceeds to Step S114.

In Step S114, the control unit 60 outputs an instruction to emit the radiation R having energy different from that in the previous imaging to the mammography apparatus 10. Specifically, in a case in which the radiation with the first energy is emitted to capture the low-energy projection image in the previous capture of the projection image, an instruction to emit the radiation R with the second energy is output to the mammography apparatus 10. In the mammography apparatus 10, the control unit 20 directs the radiation source 37R to emit the radiation R with the second energy to the breast on the basis of the instruction input from the console 12, and the radiation detector 28 captures a high-energy projection image. Further, in a case in which the radiation with the second energy is emitted to capture a high-energy projection image in the previous capture of the projection image, an instruction to emit the radiation R with the first energy is output to the mammography apparatus 10. In the mammography apparatus 10, the control unit 20 directs the radiation source 37R to emit the radiation R with the first energy to the breast on the basis of the instruction input from the console 12, and the radiation detector 28 captures a low-energy projection image.

Then, in Step S116, the control unit 60 determines whether or not the radiation source 37R is located at the end position. In this embodiment, the control unit 60 determines whether or not the radiation source 37R is located at the irradiation position $39_7$. In a case in which the radiation source 37R is not located at the end position, the determination result in Step S116 is "No", and the process returns to Step S112. Then, the processes in Steps S112 and S114 are repeated. On the other hand, in a case in which the radiation source 37R is located at the end position, the determination result in Step S116 is "No", and the process proceeds to Step S118.

Then, in Step S118, the control unit 60 stops the movement of the radiation source 37R. Then, in Step S120, the control unit 60 moves the radiation source 37R to the irradiation position $39_4$ where the irradiation angle α is 0 degrees. In a case in which the process in Step S120 ends, the imaging control process illustrated in FIG. 7 ends. In a case in which the imaging control process illustrated in FIG. 7 ends in this way, the contrast imaging ends, and the process in Step S14 illustrated in FIG. 6 ends.

Since the contrast imaging ends, the user releases the compression of the breast by the compression plate 40 as illustrated in the next Step S16.

Figure 8:
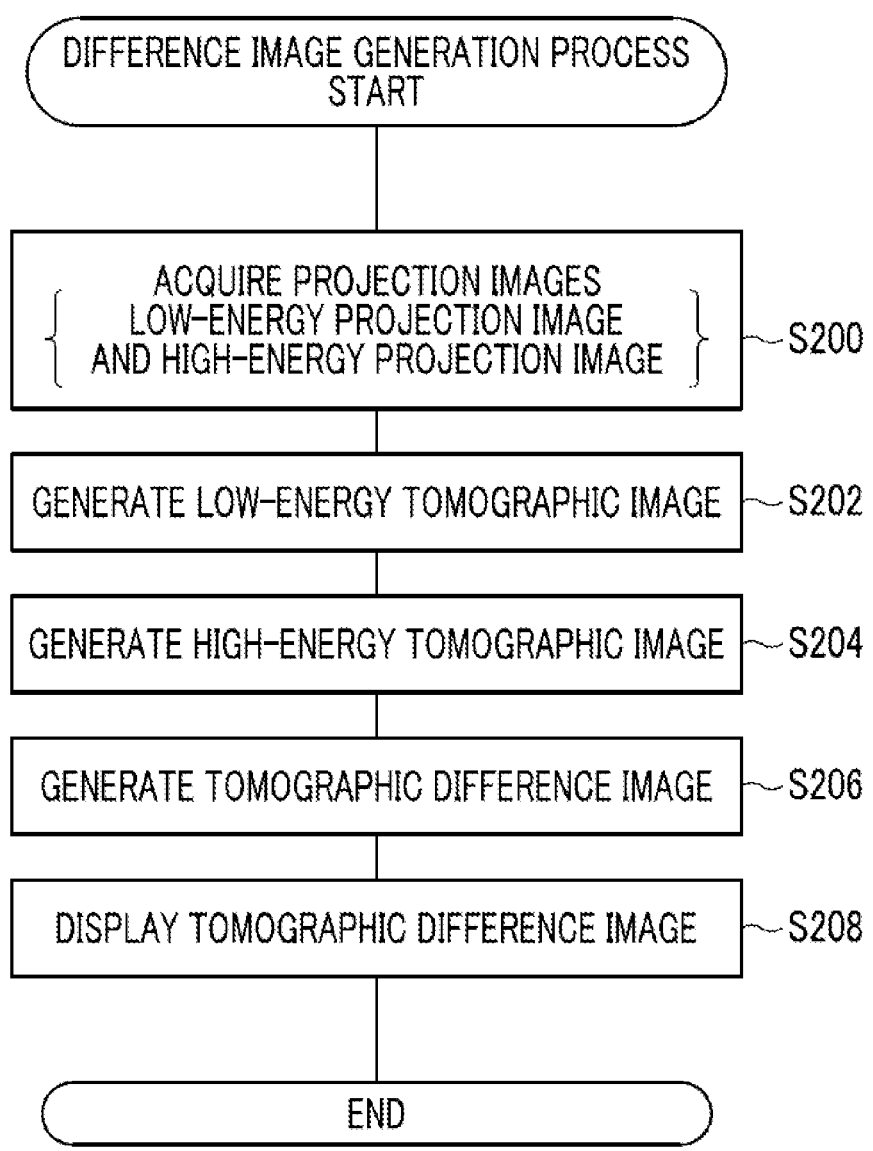
FIG. 8 is a flowchart illustrating an example of the flow of a difference image generation process.

Then, in Step S18, the console 12 performs a difference image generation process illustrated in FIG. 8. In the console 12 according to this embodiment, for example, the CPU 50A of the control unit 50 executes the difference image generation processing program 51B stored in the ROM 50B to perform the difference image generation process whose example is illustrated in FIG. 8. FIG. 8 is a flowchart illustrating an example of the flow of the difference image generation process performed in the console 12 according to this embodiment.

In Step S200, the acquisition unit 62 acquires the low-energy projection image and the high-energy projection image from the mammography apparatus 10 as described above. In addition, the timing when the acquisition unit 62 acquires the low-energy projection image and the high-energy projection image is not limited. For example, whenever each of the low-energy projection image and the high-energy projection image is captured, the low-energy projection image and the high-energy projection image may be acquired from the mammography apparatus 10. Further, for example, after the tomosynthesis imaging ends, the low-energy projection image and the high-energy projection image stored in the storage unit 22 of the mammography apparatus 10 may be acquired. Furthermore, the order in which the low-energy projection image and the high-energy projection image are acquired is not limited.

Then, in Step S202, the generation unit 64 generates a low-energy tomographic image as described above. Specifically, the generation unit 64 reconstructs the low-energy projection images (see the low-energy projection images $71L_1$ to $71L_3$ in FIG. 5) acquired in Step S200 to generate the low-energy tomographic images $74L_1$ to $74L_f$.

Then, in Step S204, the generation unit 64 generates a high-energy tomographic image as described above. Specifically, the generation unit 64 reconstructs the high-energy projection images (see the high-energy projection images $71H_1$ to $71H_4$ FIG. 5) acquired in Step S200 to generate the high-energy tomographic images $74H_1$ to $74H_f$.

Then, in Step S206, the generation unit 64 generates a tomographic difference image as described above. Specifically, the generation unit 64 generates the tomographic difference images (see the tomographic difference images $74_1$ to $74_f$ in FIG. 5) indicating the differences between the high-energy tomographic images (see the high-energy tomographic images $74H_1$ to $74H_f$ in FIG. 5) generated in Step S204 and the low-energy tomographic images (see the low-energy tomographic images $74L_1$ to $74L_f$ in FIG. 5) generated in Step S202.

Then, in Step S208, the generation unit 64 displays the tomographic difference image generated in Step S206 on the display unit 58. In addition, the generation unit 64 may display radiographic images other than the tomographic difference image on the display unit 58. For example, the generated low-energy tomographic image and high-energy tomographic image may be displayed on the display unit 58.

For example, the generation unit 64 according to this embodiment displays, on the display unit 58, the tomographic difference image subjected to a gradation enhancement process, a frequency enhancement processing, or the like. In a case in which the process in Step S208 ends, the difference image generation process illustrated in FIG. 8 ends.

In a case in which the difference image generation process illustrated in FIG. 8 ends in this way, the difference image generation process in Step S18 illustrated in FIG. 6 ends. Therefore, a series of processes related to the contrast imaging in the radiography system 1 according to this embodiment ends. In addition, the low-energy projection image and the high-energy projection image captured by the mammography apparatus 10 according to this embodiment and the low-energy tomographic image, the high-energy tomographic image, and the tomographic difference image generated by the console 12 may be stored in, for example, the storage unit 52 of the console 12 or a picture archiving and communication system (PACS).

As described above, the console 12 according to the above-described embodiment comprises the CPU 50A as at least one processor. The CPU 50A directs the mammography apparatus 10, which irradiates the breast into which the contrast medium is injected with the radiation R from the radiation source 37R to capture the radiographic image of the breast, to emit the radiation R with either the first energy or the second energy higher than the first energy at each of a plurality of irradiation positions 39 having different irradiation angles while moving the radiation source 37R to capture a plurality of low-energy projection images based on the radiation R with the first energy and a plurality of high-energy projection images based on the radiation R with the second energy. In addition, the CPU 50A performs control such that the irradiation time for which the radiation R with the second energy is emitted is longer than the irradiation time for which the radiation R with the first energy is emitted. Further, the CPU 50A performs control such that the focus size of the radiation source 37R in a case in which the radiation R with the first energy is emitted is larger than the focus size of the radiation source 37R in which the radiation R with the second energy is emitted.

As such, the console 12 according to this embodiment performs control such that the irradiation time for which the radiation R with the second energy is emitted is longer than the irradiation time for the radiation R with the first energy is emitted and the focus size in a case in which the radiation R with the first energy is emitted is larger than the focus size in a case in which the radiation R with the second energy is emitted. That is, according to the mammography apparatus 10 of this embodiment, the substantial focus size in the emission of the radiation R with the first energy is close to the substantial focus size in the emission of the radiation R with the second energy while the quality of the high-energy projection image is improved. Therefore, according to the mammography apparatus 10 of this embodiment, it is possible to suppress a difference between the degrees of blur of the low-energy projection image and the high-energy projection image. The degrees of blur of the low-energy projection image and the high-energy projection image are matched with each other to match the degrees of blur of the low-energy tomographic image and the high-energy tomographic image. Therefore, in the tomographic difference image, the blur is offset, and image quality is improved.

In addition, a method for deriving the focus size in the emission of the radiation R with the first energy in the control unit 60 is not limited to the above-described embodiment. For example, the focus size in the emission of the radiation R with the second energy may be derived on the basis of the degree of blur of the high-energy projection image obtained by imaging. For example, the amount of blur of the high-energy projection image obtained by the tomosynthesis imaging may be derived, and the focus size in the emission of the radiation R with the first energy may be derived from the derived amount of blur. In this case, a method that uses the expansion of an image by blurring is given as an example of a method for deriving the amount of blur of the high-energy projection image. As this method, the length of a predetermined marker in a high-energy projection image or a high-energy image obtained by capturing an image of the marker with the radiation source 37R fixed is obtained as an initial value. Then, the image of the predetermined marker is captured together with the breast, and the amount of blur is derived according to the difference or ratio between the length of the image of the marker included in the high-energy projection image and the initial value. In addition, in a case in which a circular marker is used, it is possible to derive the amount of blur from the aspect ratio of the image of the marker in the high-energy projection image without obtaining the initial value in advance. In a case in which the amount of blur of the high-energy projection image is obtained by obtaining the correspondence relationship with the substantial focus size in the emission of the radiation R with the second energy in advance from the amount of blur of the high-energy projection image, it is possible to derive the substantial focus size in the capture of the high-energy projection image. In a case in which the substantial focus size is obtained, it is possible to derive the focus size in the emission of the radiation R with the first energy from the moving distance of the radiation source 37R in the emission of the radiation R with the first energy. Specifically, the moving distance of the radiation source 37R in the emission of the radiation R with the first energy can be subtracted from the substantial focus size in the capture of the high-energy projection image to obtain the focus size in the emission of the radiation R with the first energy.

In addition, whether the energy of the radiation R emitted at each irradiation position 39 is the first energy or the second energy is not limited to the above-mentioned aspect. For example, in the above-described embodiment, the aspect in which the radiation R with the first energy and the radiation R with the second energy are alternately emitted at each irradiation position 39 in the tomosynthesis imaging has been described. However, the radiation may not be alternately emitted. After the radiation R with the same energy is continuously emitted at two irradiation positions 39, the radiation R with different energy may be emitted at the next irradiation position 39.

In addition, as in the above-described embodiment, it is preferable to emit the radiation R with the first energy at the irradiation position $39_4$ where the irradiation angle is 0 degrees. Since the low-energy projection image is obtained at the irradiation position $39_4$ where the irradiation angle is 0 degrees, it is possible to improve the quality of a composite two-dimensional image generated by using the low-energy tomographic image. The composite two-dimensional image is a two-dimensional image corresponding to a normal two-dimensional image captured by emitting the radiation R from the irradiation position $39_4$ where the irradiation angle is 0 degrees. For example, the composite two-dimensional image can be generated by an addition method.

In a case in which the number of imaging operations in the tomosynthesis imaging is an odd number, the radiation R with the first energy or the second energy is alternately emitted at each irradiation position 39, and the radiation R with the first energy is emitted at the irradiation position 39 where the irradiation angle is 0 degrees, the irradiation energy of the radiation R emitted at the start position is determined by the number of imaging operations, that is, the total number of irradiation positions 39. In a case in which the total number of irradiation positions 39 is 3+4×j (j=1, 2, 3, . . . ), the radiation R with the second energy is emitted at the irradiation position $39_1$ which is the start position. Further, for example, in a case in which the radiation R with the first energy and the radiation R with the second energy are alternately emitted and the total number of irradiation positions 39 is 1+4×m (m=1, 2, 3, . . . ), the radiation R with the first energy is emitted at the irradiation position $39_1$ which is the start position. In a case in which the radiation R with the first energy and the radiation R with the second energy are alternately emitted at each irradiation position 39 in odd-numbered tomosynthesis imaging operations, the energy of the radiation emitted at the start position is appropriately set according to the number of times the radiation is emitted, which makes it possible to acquire projection images which are symmetric with respect to the normal line CL as the axis and to emit the radiation R with the first energy at the irradiation position 39 where the irradiation angle is 0 degrees.

Figure 9:
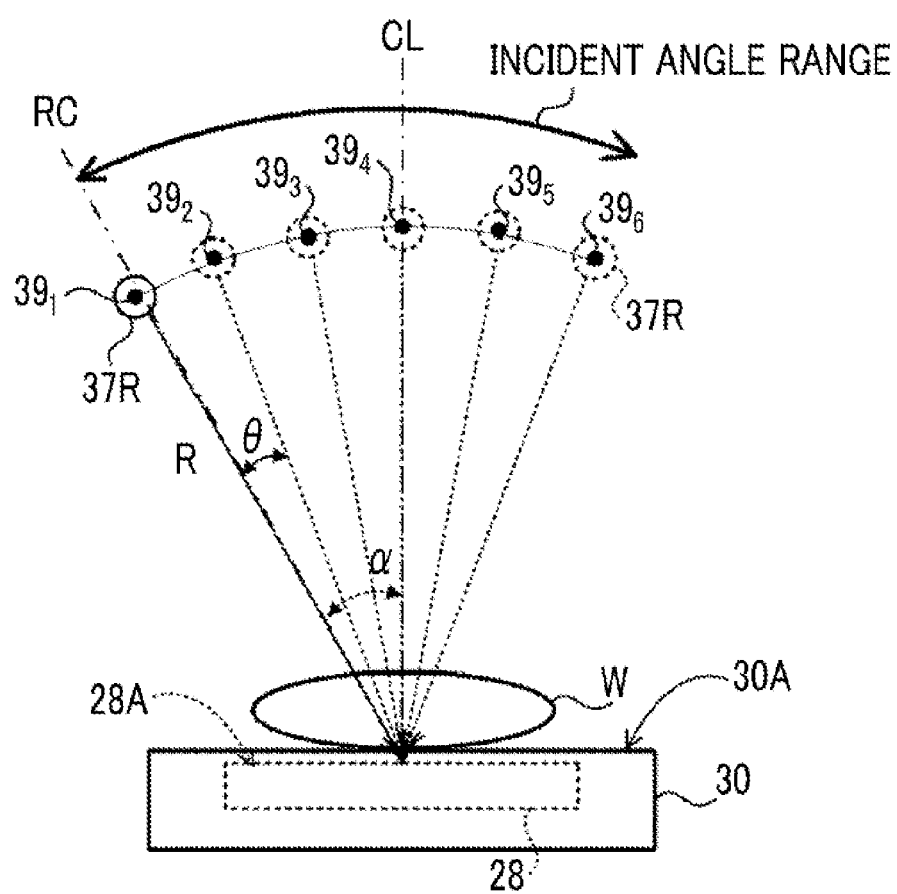
FIG. 9 is a diagram illustrating another example of the tomosynthesis imaging.

Further, in the above-described embodiment, the aspect in which the number of times the projection image is captured in the tomosynthesis imaging, specifically, the sum of the number of times the low-energy projection image is captured and the number of times the high-energy projection image is captured is an odd number. However, the sum may be an even number. In this case, the number of times the low-energy projection image is captured and the number of times the high-energy projection image is captured may be equal to each other. For example, in the example illustrated in FIG. 9, the radiation R with the second energy is emitted at the irradiation positions $39_1$, $39_3$, and $39_5$ to capture the low-energy projection images, and the radiation R with the first energy is emitted at the irradiation positions $39_2$, $39_4$, and $39_6$ to capture the high-energy projection images.

Furthermore, in the above-described embodiment, after the imaging control process which is the process in Step S14 in FIG. 6, that is, the contrast imaging ends, the difference image generation process is performed. However, the timing when the difference image generation process is performed, that is, the timing when the difference image is generated or displayed is not limited to this aspect. For example, each of the generation of the difference image and the display of the difference image may be performed at the time the user wants after the contrast imaging.

In addition, the grid included in the mammography apparatus 10 is not limited to the grid 29 in the above-described embodiment. For example, a grid in which the transmission portion 29A and the absorption portion 29B are disposed in the imaging table 30 while extending in the front-rear direction of the subject positioned on the imaging table 30 may be applied. In other words, a grid obtained by rotating the grid 29 according to this embodiment by 90 degrees may be applied. In this case, a retraction mechanism that retracts the grid from the inside of the detection surface of the radiation detector 28 to the outside of the detection surface may be provided. In a case in which two-dimensional imaging, such as the normal imaging, is performed, the grid may be inserted into the detection surface of the radiation detector 28. In a case in which the tomosynthesis imaging is performed, the grid may be retracted to the outside of the detection surface of the radiation detector 28.

Further, in the above-described embodiment, the aspect in which the console 12 is an example of the control device according to the present disclosure has been described. However, devices other than the console 12 may have the functions of the control device according to the present disclosure. In other words, for example, the mammography apparatus 10 or an external device other than the console 12 may have some or all of the functions of the control unit 60, the acquisition unit 62, and the generation unit 64.

Furthermore, in the above-described embodiment, for example, the following various processors can be used as the hardware structure of processing units performing various processes such as the control unit 60, the acquisition unit 62, and the generation unit 64. The various processors include, for example, a programmable logic device (PLD), such as a field programmable gate array (FPGA), that is a processor whose circuit configuration can be changed after manufacture and a dedicated electric circuit, such as an application specific integrated circuit (ASIC), that is a processor having a dedicated circuit configuration designed to perform a specific process, in addition to the CPU that is a general-purpose processor which executes software (program) to function as various processing units as described above.

One processing unit may be configured by one of the various processors or a combination of two or more processors of the same type or different types (for example, a combination of a plurality of FPGAs or a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

In addition, specifically, an electric circuit (circuitry) obtained by combining circuit elements, such as semiconductor elements, can be used as the hardware structure of the various processors.

Further, in the above-described embodiment, the aspect in which the imaging control processing program 51A and the difference image generation processing program 51B are stored (installed) in the ROM 50B in advance has been described. However, the present disclosure is not limited thereto. The imaging control processing program 51A and the difference image generation processing program 51B may be recorded on a recording medium, such as a compact disc read only memory (CD-ROM), a digital versatile disc read only memory (DVD-ROM), or a universal serial bus (USB) memory, and then provided. Further, each of the imaging control processing program 51A and the difference image generation processing program 51B may be downloaded from an external device through a network.

What is claimed is:

1. A control device comprising:
   at least one processor,
   wherein the processor controls a mammography apparatus that irradiates a breast, into which a contrast medium is injected, with radiation from a radiation source to capture a radiographic image of the breast such that the radiation with either first energy or second energy higher than the first energy is emitted at each of a plurality of irradiation positions having different irradiation angles while the radiation source is being moved to capture a plurality of low-energy projection images based on the radiation with the first energy and a plurality of high-energy projection images based on the radiation with the second energy, an irradiation time for which the radiation with the second energy is emitted is longer than an irradiation time for which the radiation with the first energy is emitted, and a focus size of the radiation source in a case in which the radiation with the first energy is emitted is larger than a focus size of the radiation source in a case in which the radiation with the second energy is emitted.

2. The control device according to claim 1, wherein the processor performs control such that a substantial focus size in a case in which the radiation with the first energy is emitted is equal to a substantial focus size in a case in which the radiation with the second energy is emitted.

3. The control device according to claim 2, wherein the substantial focus size is determined by the focus size of the radiation source, a movement speed of the radiation source, and the irradiation time of the radiation.

4. The control device according to claim 1, wherein the plurality of irradiation positions include an irradiation position where the irradiation angle along a normal direction to an imaging table on which the breast is positioned is 0 degrees, and
   the processor performs control such that the radiation with the first energy is emitted at the irradiation position where the irradiation angle is 0 degrees.

5. The control device according to claim 1, wherein the processor performs control such that the radiation with the second energy is emitted at an irradiation position which is a start position among the plurality of irradiation positions to capture the high-energy projection image and derives the focus size of the radiation source in a case in which the radiation with the first energy is emitted from an amount of blur of the high-energy projection image.

6. The control device according to claim 1, wherein the processor acquires the plurality of low-energy projection images and the plurality of high-energy projection images and generates tomographic difference images indicating differences between high-energy tomographic images generated by reconstructing the plurality of high-energy projection images and low-energy tomographic images generated by reconstructing the plurality of low-energy projection images.

7. A control method comprising:
   controlling a mammography apparatus that irradiates a breast, into which a contrast medium is injected, with radiation from a radiation source to capture a radiographic image of the breast such that the radiation with either first energy or second energy higher than the first energy is emitted at each of a plurality of irradiation positions having different irradiation angles while the radiation source is being moved to capture a plurality of low-energy projection images based on the radiation with the first energy and a plurality of high-energy projection images based on the radiation with the second energy, an irradiation time for which the radiation with the second energy is emitted is longer than an irradiation time for which the radiation with the first energy is emitted, and a focus size of the radiation source in a case in which the radiation with the first energy is emitted is larger than a focus size of the radiation source in a case in which the radiation with the second energy is emitted.

8. A non-transitory computer-readable storage medium storing a control program that causes a computer to perform a process of:
   controlling a mammography apparatus that irradiates a breast, into which a contrast medium is injected, with radiation from a radiation source to capture a radiographic image of the breast such that the radiation with either first energy or second energy higher than the first energy is emitted at each of a plurality of irradiation positions having different irradiation angles while the radiation source is being moved to capture a plurality of low-energy projection images based on the radiation with the first energy and a plurality of high-energy projection images based on the radiation with the second energy, an irradiation time for which the radiation with the second energy is emitted is longer than an irradiation time for which the radiation with the first energy is emitted, and a focus size of the radiation source in a case in which the radiation with the first energy is emitted is larger than a focus size of the radiation source in a case in which the radiation with the second energy is emitted.

* * * * *